(12) United States Patent
Al-Lamee et al.

(10) Patent No.: US 8,252,732 B2
(45) Date of Patent: Aug. 28, 2012

(54) HYDROPHILIC SURFACES FOR REDUCING FRICTION FORCES

(75) Inventors: Kadem Al-Lamee, Didcot (GB); Sam Patrick Whitehouse, Didcot (GB)

(73) Assignee: Bayer MatrialScience AG, Leverkusen (DE)

( * ) Notice: Subject to any disclaimer, the term of this patent is extended or adjusted under 35 U.S.C. 154(b) by 409 days.

(21) Appl. No.: 12/440,385

(22) PCT Filed: Aug. 23, 2007

(86) PCT No.: PCT/GB2007/003209
§ 371 (c)(1), (2), (4) Date: Dec. 22, 2009

(87) PCT Pub. No.: WO2008/029082
PCT Pub. Date: Mar. 13, 2008

(65) Prior Publication Data
US 2010/0087343 A1    Apr. 8, 2010

(30) Foreign Application Priority Data
Sep. 7, 2006   (GB) .................................. 0617644.0

(51) Int. Cl.
*F16C 33/04*   (2006.01)
*A61L 33/00*   (2006.01)

(52) U.S. Cl. ............... 508/100; 427/2.1; 427/256
(58) Field of Classification Search ............. 508/100; 522/84, 150, 151, 152, 173, 175; 525/374, 525/452; 427/2.1
See application file for complete search history.

(56) References Cited

U.S. PATENT DOCUMENTS

| | | | |
|---|---|---|---|
| 5,618,887 A * | 4/1997 | Bamford et al. | 525/279 |
| 6,369,168 B1 * | 4/2002 | Al-Lamee et al. | 525/376 |
| 2007/0224236 A1 * | 9/2007 | Boden | 424/423 |
| 2009/0012208 A1 * | 1/2009 | Madsen et al. | 523/113 |

FOREIGN PATENT DOCUMENTS

| | | |
|---|---|---|
| GB | 2324530 A | 10/1998 |
| WO | WO9325587 A | 12/1993 |

OTHER PUBLICATIONS

European Search Report, EP 10 19 3570.8-2102, May 27, 2011.

* cited by examiner

*Primary Examiner* — Ellen McAvoy
*Assistant Examiner* — Vishal Vasisth
(74) *Attorney, Agent, or Firm* — Joseph T. Leone, Esq.; Daniel A. Blasiole; Dewitt Ross & Stevens, S.C.

(57) ABSTRACT

A substrate (for example an implantable medical device) is provided with a lubricious surface by grafting onto the surface monomers containing acrylamide groups and then hydrolyzing said groups under alkaline conditions, the grafting step being carried out in an aqueous environment.

14 Claims, 1 Drawing Sheet

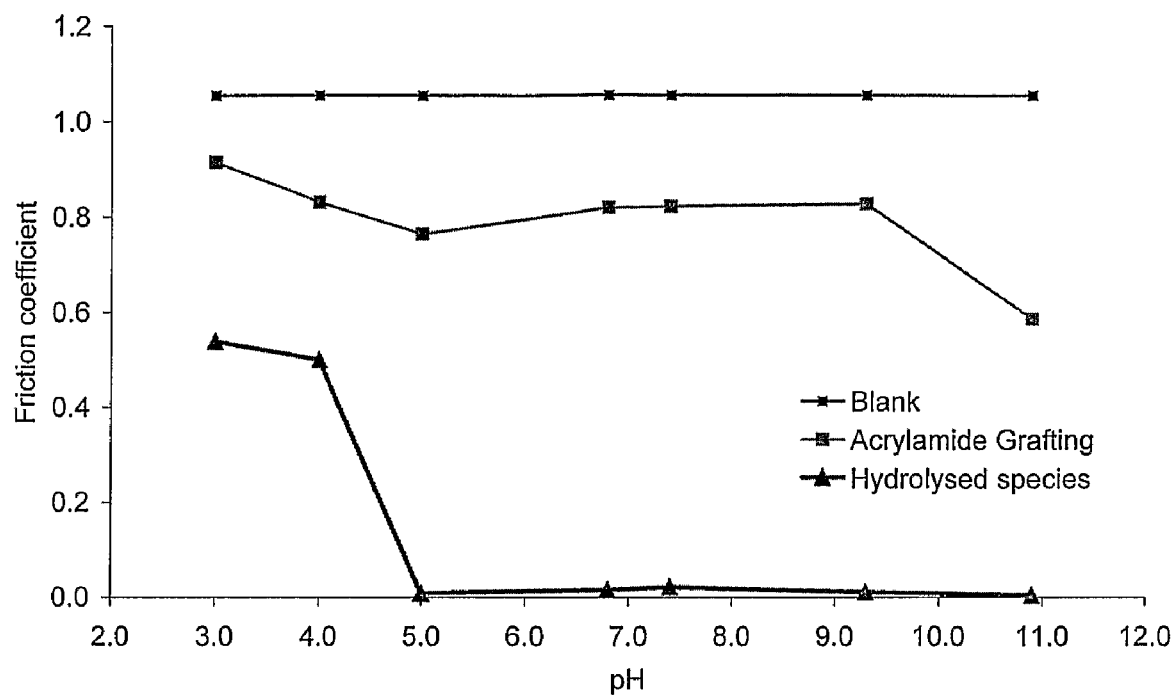

HYDROPHILIC SURFACES FOR REDUCING FRICTION FORCES

This application is a 371 of PCT/GB2007/003209, filed Aug. 23, 2007, which claims priority to GB Application Ser. No. 0617644.0, filed 7 Sep. 2006, both of which are incorporated herein.

This invention relates to a method of forming a lubricious hydrophilic coating using aqueous media on a variety of polymeric substrates such as polyamides, polyurethanes, polyesters, polycarbonates. As this invention uses aqueous media the modification can also be applied to the internal lumen of tubing of such substrates.

In the main this technology has been developed for use for medical applications but is not limited to this application and in principle can be applied to any polymeric substrate.

The formation of hydrophilic coatings on substrates has many applications, in particular medical devices. These devices are intended for insertion into the body and be easily handled when dry but to become lubricious on contact with water, or when placed in an aqueous environment. The device can then be inserted into or removed from the patient without causing unnecessary additional damage.

When a device such as a percutaneous transluminal coronary angioplasty (PTCA) catheter, neuro-catheter or guidewire is inserted into the artery there is a tendency for the device to cause damage to the arterial wall whilst being manipulated to the site of interest. This additional damage is commonly caused when the catheter is required to negotiate tight angles such as those found in the heart. It is also commonplace to find that devices with high coefficients of friction cannot be deployed to more tortuous regions in the body. By reducing the friction between the device and the arterial wall this will in turn reduce the excess damage caused when such a procedure is performed and allow access to more tortuous vessels.

U.S. Pat. No. 3,895,169 (Ceskoslovenska akademie) discloses a method of converting the surface of a non-hydrophilic acrylic resin to form a hydrophilic layer thereon by using a strong acid to hydrolyse ester, amide or nitrile groups at the surface and a hydroxyl compound is then used to re-esterify the surface to result in a hydrophilic surface layer.

Another reference in which the surface of an implant is made more hydrophilic is U.S. Pat. No. 4,026,296 (Ceskoslovenska akademie). This discloses a surgical device formed of a hydrophilic copolymer of acrylonitrile with either acrylamide or acrylic acid. The hydrophilic properties of the surface can be increased by either changing the degree of hydrolysis (if the copolymer was prepared by partial hydrolysis of the polyacrylonitrile) or by changing the content of the hydrophilic units (if the copolymer was prepared by copolymerisation of a monomer mixture).

WO 98/55172 (Scimed) discloses a method of forming a surface on a medical implant comprising coating the implant with a maleic anhydride copolymer and then altering the lubricity of the surface by differential hydrolysis of the anhydride groups followed by neutralisation of the resulting acid groups.

In accordance with a first aspect of the present invention, there is provided a method of providing a substrate with a lubricious surface, including the steps of grafting onto the substrate in an aqueous environment a monomer containing an acrylamide functional group (such as acrylamide itself or N-N dimethylacrylamide) and then hydrolysing said functional group in alkaline conditions.

Preferably the method comprises the steps of:
(i) Activating the surface of the device using either a chemical activation or a physical treatment such as plasma treatment, a corona discharge or an ozone treatment that is produced as a by-product with these treatments.
(ii) Grafting onto the surface a monomer that is then bound covalently to the surface
(iii) Converting the grafted monomer by chemical methods, such as hydrolysis, to increase the hydrophilic properties and thereby increasing lubricity, and lowering the friction forces.

Activation of surfaces using treatments such as plasma treatment, corona discharge or ozone treatment is a common method for increasing the wettability of polymer surfaces using an electrical discharge. Activation of the surface of a polymer in this way creates a high energy surface that is able to increase adhesion of materials such as inks, glues and coatings. Chemical activation can also be used to activate the surface ready to graft a polymer onto the surface. Such methods include the use of peroxy disulphates or mono sulphates or the use of water soluble azo compounds to produce hydroxyl radicals from the decomposition of the oxidising agents. These methods have been previously described in European patent publication number EP 0643730 (The University of Liverpool) and U.S. Pat. No. 6,369,168 B1 (PolyBioMed Limited).

The grafting of vinyl monomers such as acrylamide or derivatives thereof forming polyacrylamide onto activated surfaces is a common procedure. Often the use of chemical initiators such as metal oxidising compounds (one example being ammonium cerium nitrate) is used to initiate the polymerisation process in monomer solutions. This, in combination with the activated surface, results in the polymer being covalently bound to the surface of the device. It has previously been shown in patent publication U.S. Pat. No. 6,599,558 B1 (PolyBioMed Limited) that the grafting of acrylamide monomers can also be performed on metallic substrates via the formation of a suitably reactive surface, containing at least one group that that can participate in free-radical polymerisation.

Once the grafting procedure has taken place and the polymer is attached to the surface it is then possible to partially or fully convert the functional groups of the grafted polymer in order to adapt the overall properties exhibited. In this invention by converting the functional groups of the grafted polymer the device shows a decrease in the friction forces.

The method of the present invention may be used to treat any part of a substrate. For example, it may be used to treat the internal surface of the lumen of a medical device (such as a stent graft). It may also be used to treat only part of a substrate. In a preferred embodiment areas of a substrate which are not to be treated may be masked with, for example, a non-reactive polymer which can be removed after the remainder of the substrate has been provided with a lubricious surface.

Brief description of the drawing: FIG. 1 depicts coefficients of friction on Pebax® tubing at a range of pH conditions for non-treated tubing, tubing after grafting acrylamide thereto, and tubing after grafting acrylamide thereto and hydrolysing the grafted acrylamide.

EXAMPLES

A number of preferred embodiments of the present invention will now be described by way of example.

A polymer surface of a PTCA catheter is activated by way of corona discharge, having been cleaned of all possible surface contaminants. The activated polymer is then submerged into a monomer solution containing a suitable oxidising agent to initiate the polymerisation process. Once the polymerisation process has grafted the new polymer to the surface, it is then removed from the solution, washed and the functional groups converted to promote surface lubricity.

Materials
Isopropanol: Sigma Aldrich
Corona Discharge & Ozone generation:
 Tantec EST system—bench top corona treatment system
Deionised water
Acrylamide: Sigma Aldrich
Ammonium cerium nitrate: Sigma Aldrich
Nitric acid: BDH
Sodium hydroxide: BDH
Harland Medical FTS5000 friction force tester Comparative Example 1

Conventional Method

A PTCA catheter is cleaned with isopropanol and allowed to dry at room temperature The PTCA catheter is then treated with a corona discharge over the full length of the catheter, on both sides, to ensure complete activation of the surface.

A solution of 5% w/v acrylamide and 1% w/v (1 molar) nitric acid in deionised water is degassed with nitrogen to remove oxygen (a retardant in the polymerisation process) and brought to 40° C. The activated catheter is then placed into the solution and the reaction is started immediately with the addition of 0.2% w/v ammonium cerium nitrate. The reaction is then allowed to proceed under nitrogen flow until no colour is detected from the ammonium cerium nitrate.

The catheter is removed and washed to remove unwanted contaminants.

Example 2

Conversion to Acid Salt

Grafting of the PTCA catheter with acrylamide is carried out using the method from Example 1.

The catheter is then placed in a 1 molar solution of sodium hydroxide at 40° C. to convert the bound polyacrylamide to the acid. The catheter is then removed from the solution and washed with deionised water.

The table below shows the relative increase in lubricity, via push and pull forces, at different stages of the process.

Values given are the force (in grams) taken to push or pull a sample through a clamp with a force of 450 grams applied to it. The Coefficient of Friction is force taken to move a sample through this clamp divided by the force that is applied by the clamp.

| Sample | Average Push Force, gf | Average Pull force, gf |
|---|---|---|
| Non Coated | 52 | 90 |
| Grafted Polyacrylamide | 72 | 61 |
| Hydrolysed Grafted Polyacrylamide | 12 | 29 |

The simple grafting of the acrylamide to the surface shows no reduction in the overall friction force of the coating (although the pull force is slightly reduced). The conversion of acrylamide to the acid shows a 77% reduction in the push force.

Comparative Example 3

A length of Pebax® tube is cleaned with isopropanol and allowed to dry at room temperature (Pebax® is a polyether block amide thermoplastic elastomer produced by Arkema Inc.).

The Pebax® tubing is then treated with a corona discharge (Tantec EST system—bench top corona treatment system) over the full length of the tubing, on both sides, to ensure complete activation of the surface. The sample is then left in an ozone atmosphere for 10 minutes to ensure surface activation.

A solution of 5% w/v acrylamide and 1% w/v (1 molar) nitric acid in deionised water is degassed with nitrogen to remove oxygen (a retardant in the polymerisation process) and brought to 50° C. The reaction is started immediately with the addition of 0.2% w/v ammonium cerium nitrate and the activated Pebax® tubing is then placed into the solution. The reaction is then allowed to proceed under nitrogen flow until no colour is detected from the ammonium cerium nitrate.

The catheter is removed and washed to remove unwanted contaminants.

The catheter is then placed in a 1 molar solution of sodium hydroxide at 50° C. to convert the bound polyacrylamide to the acid salt. The catheter is then removed from the solution and washed with deionised water.

In order to obtain friction force data the sample is placed in varying pH conditions and PBS buffer (pH 7.4) and tested on a Harland Medical FTS5000 friction force tester.

Friction forces are outlined below for non-treated tubing, tubing after the first step (grafted acrylamide) and the final product (hydrolysed species). Clamp force used=450 g. The results are shown in Table 1 below and in FIG. 1:

TABLE 1

| pH | Blank | Acrylamide Grafting | Hydrolysed species |
|---|---|---|---|
| 3.0 | 1.056 | 0.915 | 0.538 |
| 4.0 | 1.056 | 0.831 | 0.500 |
| 5.0 | 1.056 | 0.765 | 0.008 |
| 6.8 | 1.056 | 0.820 | 0.016 |
| 7.4 | 1.056 | 0.822 | 0.021 |
| 9.3 | 1.056 | 0.828 | 0.010 |
| 10.9 | 1.056 | 0.586 | 0.004 |

Table 2 below illustrates the friction values obtained by this process for a variety of materials commonly used in the medical device industry:

TABLE 2

| Material | Unmodified Average Pull Force (grams) | Unmodified Average CoF | Modified Average Pull Force (grams) | Modified Average CoF |
|---|---|---|---|---|
| PA12 | 475.2 | 1.056 | 16.9 | 0.037 |
| PU | 217.5 | 0.483 | 7.9 | 0.017 |
| Pebax 5533 | 475.2 | 1.056 | 7.2 | 0.016 |
| PA12/Pebax copolymer | 475.2 | 1.056 | 17.4 | 0.038 |
| 316L Metal reinforced Pebax | 475.2 | 1.056 | 21.8 | 0.048 |
| Pigmented Pebax | 475.2 | 1.056 | 10.6 | 0.023 |

The invention claimed is:

1. A method of providing a substrate with a lubricious surface on only a part of the substrate, including the steps of grafting onto only the part of the substrate in an aqueous environment a monomer containing an acrylamide functional group and then hydrolysing said functional group in alkaline conditions in order further to increase the lubricious nature of said surface, wherein the part of the substrate which is not to be treated is masked with a non-reactive polymer which is removed at the end of the method, wherein the substrate is a medical device.

2. A method as claimed in claim 1 wherein the monomer is acrylamide or N-N dimethylacrylamide.

3. A method as claimed in claim 1 wherein prior to the grafting step the surface of the substrate is activated to increase adhesion of the polymer.

4. A method as claimed in claim 3 wherein the activation is carried out by means of a plasma treatment, corona discharge, ozone treatment or by chemical activation.

5. A method as claimed in claim 3 wherein the surface activation results in hydroxyl groups being formed at the surface of the substrate.

6. A method as claimed in claim 1 wherein the substrate is formed from a polyether block amide.

7. A method as claimed in claim 1 additionally comprising the step of attaching a bioactive to the hydrolysed functional group.

8. A method of providing a substrate with a lubricious surface, including the steps of masking a first part of the substrate with a non-reactive polymer, grafting onto only a second part of the substrate in an aqueous environment a monomer containing an acrylamide functional group, hydrolysing said functional group in alkaline conditions in order further to increase the lubricious nature of said surface, and then removing the non-reactive polymer, wherein the substrate is a medical device.

9. A method as claimed in claim 8 wherein the monomer is acrylamide or N-N dimethylacrylamide.

10. A method as claimed in claim 8 wherein prior to the grafting step the surface of the substrate is activated to increase adhesion of the polymer.

11. A method as claimed in claim 10 wherein the activation is carried out by means of a plasma treatment, corona discharge, ozone treatment or by chemical activation.

12. A method as claimed in claim 10 wherein the surface activation results in hydroxyl groups being formed at the surface of the substrate.

13. A method as claimed in claim 8 wherein the substrate is formed from a polyether block amide.

14. A method as claimed in claim 8 additionally comprising the step of attaching a bioactive to the hydrolysed functional group.

* * * * *